United States Patent [19]

Rohr, Jr.

[11] Patent Number: 5,658,348
[45] Date of Patent: Aug. 19, 1997

[54] ACETABULAR IMPLANT WITH THREADED LINER AND LOCKING RING

[75] Inventor: William L. Rohr, Jr., Warsaw, Ind.

[73] Assignee: Bristol-Myers Squibb Company, New York, N.Y.

[21] Appl. No.: 708,421

[22] Filed: Sep. 9, 1996

[51] Int. Cl.$^6$ ..................................................... A61F 2/34
[52] U.S. Cl. ................................. 623/22; 623/18; 623/19
[58] Field of Search .................................. 623/18, 19, 22, 623/23

[56] References Cited

U.S. PATENT DOCUMENTS

| | | | |
|---|---|---|---|
| 4,681,589 | 7/1987 | Tronzo | 623/22 |
| 4,695,282 | 9/1987 | Forte et al. | 623/22 |
| 4,878,918 | 11/1989 | Tari et al. | 623/22 |
| 4,919,674 | 4/1990 | Schelhas | 623/22 |
| 5,021,062 | 6/1991 | Adrey et al. | 623/22 |
| 5,108,447 | 4/1992 | Zeiler et al. | 623/22 |
| 5,383,938 | 1/1995 | Rohr et al. | 623/22 |

Primary Examiner—David Isabella
Attorney, Agent, or Firm—Todd A. Dawson

[57] ABSTRACT

The acetabular implant of the invention includes a shell having a threaded polar hole with a liner having a threaded polar protrusion extending therefrom for threadable accommodation within the threaded polar hole. Further, the implant includes a locking ring carried by the shell for engagement with the liner. In use, the liner is screwed into the shell by the cooperating threads of the liner and shell. As the liner bottoms out in the shell, the locking ring slides into an annular groove formed in the outer periphery of the shell to lock the liner to the shell. The locking engagement of the locking ring prevents the liner from shifting laterally relative to the shell which therefore prevents the liner from rotating in a direction to loosen the shell relative to the liner. While it is preferred that the liner is formed from a metal, the liner may be formed from either a metal or a plastic dependant upon the clinical requirements for the patient.

3 Claims, 1 Drawing Sheet

ACETABULAR IMPLANT WITH THREADED LINER AND LOCKING RING

FIELD OF THE INVENTION

This invention relates to prosthetic acetabular implants and has specific relevance to an acetabular implant having a liner which is screwed into its shell such that as the screw threads bottom out an annular locking ring engages the liner to prevent the liner from rotating in an opposite direction.

SUMMARY OF THE INVENTION

It is known to have an acetabular cup having a shell and a liner held in engagement by a locking ring. It is further known to provide a threaded polar hole in the shell to theadibly connect the shell to an impaction component. It is further known to have a polyethylene liner formed having a polar protrusion for press fitting into the polar hole. The present invention includes a shell having a threaded polar hole with a liner having a threaded polar protrusion extending therefrom for threadable accommodation within the threaded polar hole. Further, the invention includes a locking ring carded by the shell for engagement with the liner. In use, the liner is screwed into the shell by the cooperating threads of the liner and shell. As the liner bottoms out in the shell, the locking ring slides into an annular groove formed in the outer periphery of the shell to lock the liner to the shell. The locking engagement of the locking ring prevents the liner from shifting laterally relative to the shell which therefore prevents the liner from rotating in a direction to loosen the shell relative to the liner. While it is preferred that the liner is formed from a metal, the liner may be formed from either a metal or a plastic dependant upon the clinical requirements for the patient.

Accordingly, it is an object of the invention to provide for a novel prosthetic acetabular cup having a threaded polar hole in the shell and a mating threaded polar protrusion from the liner.

Another object of the invention is to provide for an acetabular cup having a shell with a threaded polar hole and a liner with mating threaded protrusion and further including a locking ring which is carded by the shell and engages the liner when the threaded protrusion of the liner bottoms out within the threaded polar hole of the shell.

Other objects of the invention will become apparent upon a reading of the following description taken with the accompanying drawings.

DESCRIPTION OF THE PREFERRED EMBODIMENT

Figure 2:
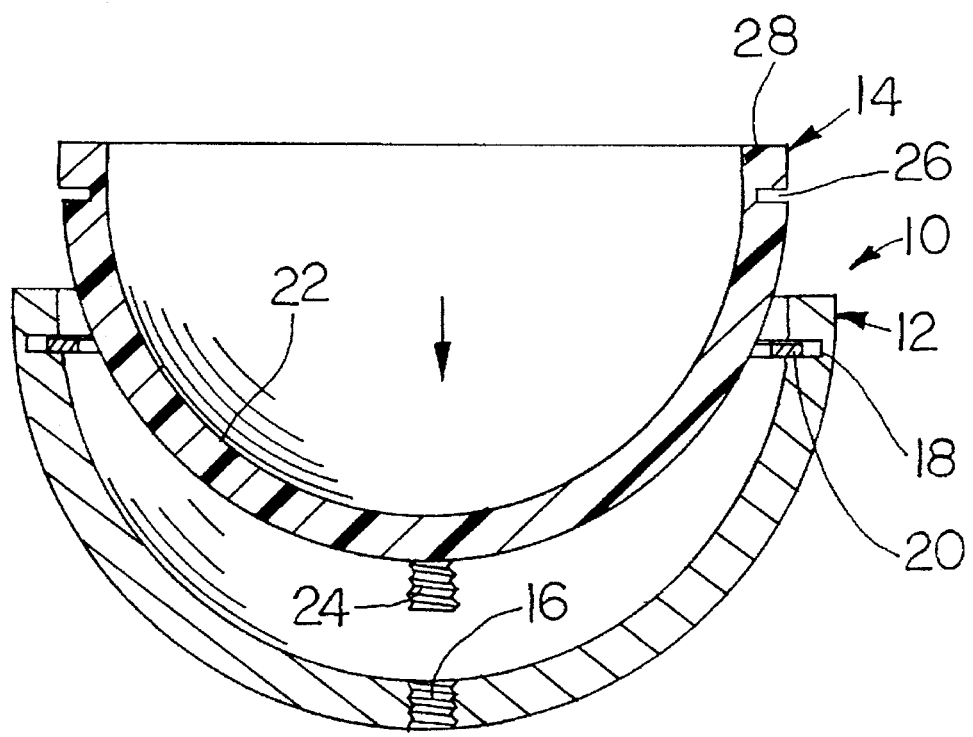
FIG. 2 is an exploded sectional view of the acetabular cup of the invention.
Figure 1:
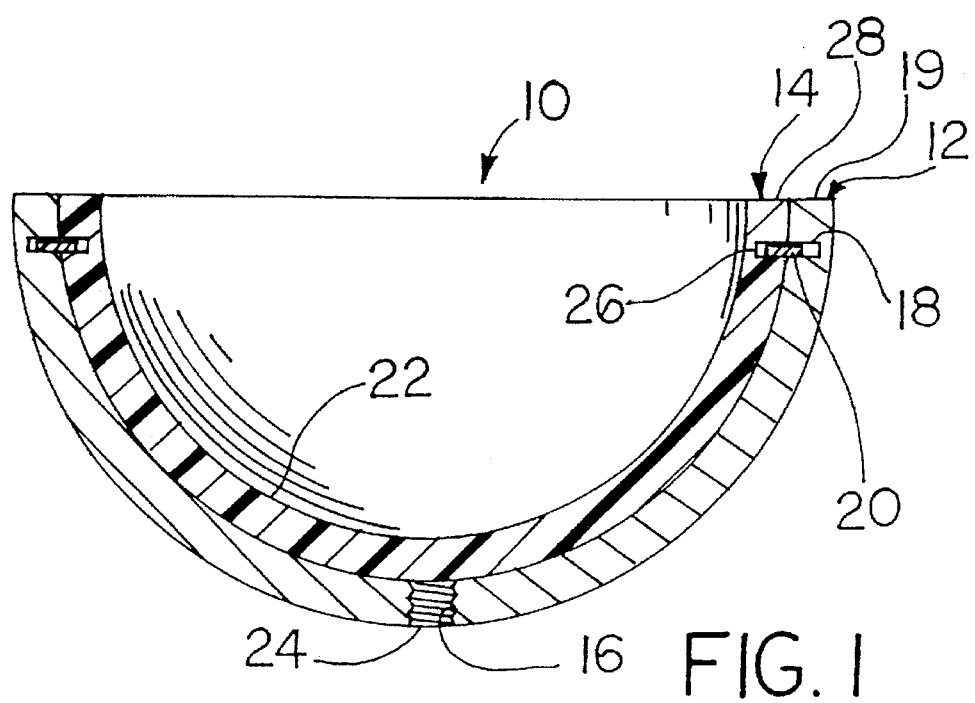
FIG. 1 is a sectional view of an acetabular cup of the invention.

The description of the preferred embodiment herein described is not intended to be exhaustive or to limit the invention to the precise form disclosed. Rather, it is chosen and described in order to best explain the invention so that others skilled in the art might utilize its teachings.

As illustrated in the figures, the prosthetic acetabular cup 10 of the invention includes a shell 12 and a liner 14. While it should not be considered a limitation, shell 12 and liner 14 are substantially hemispherical in shape. Shell 12 includes a polar threaded hole 16 and an annular groove 18 formed near its equatorial edge 19. A locking ring 20 is partially seated within groove 18 so as to extend partially into the interior of shell 12. Shell 12 is configured for contact and fixation within the prepared acetabulum of a patient. Therefore, while it is not shown, shell 12 may include a number of known exterior surface treatments such as a coating of hydroxyapatite or a porous surface layer. Further, a plurality of holes may be formed through shell 12 to accommodate fixation screws to secure the shell to the acetabulum. Liner 14 is configured to seat within shell 12 and includes an interior articulate surface 22 adapted to contact a prosthetic acetabular head. Liner 14 includes a threaded polar protrusion 24 having threads which mate with the threads of the polar hole 16 of shell 12. Finally, liner 14 includes an annular groove 26 formed about the periphery of the shell adjacent its equatorial edge 28.

In use, after the shell 12 is seated and fixed within a prepared acetabulum, the surgeon installs liner 14 by first screwing the polar protrusion 24 of liner 14 into polar hole 16 of liner 14. As the liner is turned into the shell, the exterior periphery of liner 14 presses against lock ring 20 to move it in a lateral direction and further into groove 18. When the threaded protrusion is fully seated within the bore, at least some portion of the exterior surface 23 of the liner fully registers with the inner surface 17 of the shell. At this time, groove 26 of liner 14 is aligned with lock ring 20 which resumes its normal position and forms an interference between the shell and liner. In this manner, if the shell attempts to loosen, the lock ring will prevent the liner from shifting away from the shell.

It should be understood that the shell is typically made from a biocompatible metal such as cobalt-chromium or titanium alloys and that the liner is typically formed from a polymer material such as ultra high molecular weight polyethylene, however, such should not be considered a limitation on the invention. For example, it may be advantageous to form the liner from a biocompatible metal or ceramic. Forming the liner from metal may provide a way for the manufacturer to reduce costs associated with the production of implants or of combining the most biocompatible shell with the best wearing liner.

Further, it should be understood that the invention is not to be limited to the details above but may be modified within the keeping of the appended claims.

I claim:

1. A prosthetic acetabular implant comprising;

an outer shell having an exterior surface configured for contact with an acetabulum and an interior surface adapted to receive a liner, said shell including a threaded polar hole, said shell further including an annular groove formed in the inner surface of the shell adjacent an edge of the shell, a locking ring partially seated within the annular groove of the shell and extending outwardly therefrom; and a liner having an interior surface configured for contact with a prosthetic femoral head and an exterior surface adapted to register with the interior surface of the shell, said liner further including a polar protrusion having external threads and configured for threaded engagement with the polar hole of the shell, said liner further including an annular groove formed in the exterior surface of the liner adjacent an edge thereof;

wherein as said polar protrusion of said liner is screwed into the polar hole of said shell, the exterior surface of the liner contacts the lock ring to urge the lock ting into the groove formed in the shell until said exterior surface of the liner registers with the interior surface of the shell wherein the groove formed within the exterior of the liner is aligned with the groove formed in the shell such that the lock ring extends into the groove of the shell sufficient to form an interference between the liner and shell to prevent said liner from shifting away from the shell.

2. The prosthetic acetabular implant of claim 1 wherein said shell is formed from a biocompatible metal and said liner is formed from a polymer material.

3. The prosthetic acetabular implant of claim 1 wherein said shell and said liner are formed from biocompatible metal.

* * * * *